United States Patent [19]

Lin et al.

[11] Patent Number: 4,904,654

[45] Date of Patent: Feb. 27, 1990

[54] 7-CHLORO-5,6-DIHYDRO-3-(5-(2-HYDROXY-ISOPROPYL)-1,2,4-OXADIAZOL-3-YL)-5-METHYL-6-OXO-4H-IMIDAZO[1,5A][1,4]BENZODIAZEPINE

[75] Inventors: Jiunn H. Lin, Ambler; Steven M. Pitzenberger; Harri G. Ramjit, both of Lansdale; Edgar H. Ulm, Green Lane, all of Pa.

[73] Assignee: Merck & Co., Inc., Rahway, N.J.

[21] Appl. No.: 385,039

[22] Filed: Jul. 26, 1989

[51] Int. Cl.$^4$ .................. C07D 487/04; A01K 31/55
[52] U.S. Cl. ..................................... 514/220; 548/498
[58] Field of Search ........................ 540/498; 514/220

[56] References Cited

U.S. PATENT DOCUMENTS 4,507,313  3/1985  Braestrup et al. .................. 514/220
4,775,671  10/1988  Hunkeler ............................. 514/220

FOREIGN PATENT DOCUMENTS 241682  10/1987  European Pat. Off. ............ 540/498

Primary Examiner—Robert Gerstl
Attorney, Agent, or Firm—William H. Nicholson; Joseph F. DiPrima

[57] ABSTRACT

A metabolite of the known anxiolytic agent, 7-chloro-5,6-dihydro-3-(5-isopropyl-1,2,4-oxadiazol-3-yl)-5-methyl-6-oxo-4H- imidazo[1,5a][1,4]benzodiazepine is a 2-hydroxy derivative of the isopropyl moiety and is itself an anxiolytic agent.

3 Claims, No Drawings

7-CHLORO-5,6-DIHYDRO-3-(5-(2-HYDROXY-ISO-PROPYL)-1,2,4-OXADIAZOL-3-YL)-5-METHYL-6-OXO-4H-IMIDAZO[1,5A][1,4]BENZODIAZEPINE

SUMMARY OF THE INVENTION

This invention is concerned with the title compound of structural formula:

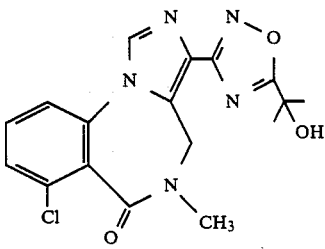

which is an anxiolytic agent. It was first discovered as a mammalian metabolite of the anxiolytic agent of structural formula:

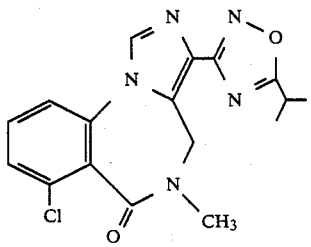

which is generically described in U.S. Pat. No. 4,507,313. The metabolite has since been synthesized and also shown to be active as an anxiolytic agent.

The invention is also concerned with a novel process for synthesis of the novel compound; pharmaceutical formulations thereof; and a method of treating anxiety therewith.

BACKGROUND OF THE INVENTION

The benzodiazepines have formed an important class of anxiolytic agents for several years. Recently there have been publications such as U.S. Pat. Nos. 4,507,313 and 4,775,671 on the sub-group of the class, known as the imidazobenzodiazepines, particularly in which the imidazo group is substituted with an alkyloxadiazole group.

Now with the present invention there is provided a hydroxy derivative of an important member of that subgroup which is also active as an anxiolytic agent.

DETAILED DESCRIPTION OF THE INVENTION

This invention is concerned with the novel compound of structural formula:

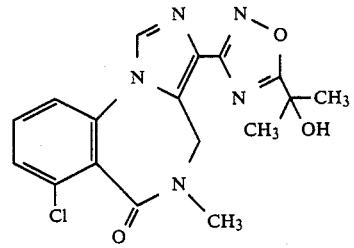

or pharmaceutically acceptable salt thereof.

This compound a metabolite of the above-identified substrate was isolated from the urine of laboratory animals, partially purified and analyzed by mass spectrometric techniques such as EI and FAB/MS. The results of these experiments are summarized in Table I.

The absolute identity of the Compound was established from High Resolution Exact mass measurements summarized in Table II while hydroxylation was verified from the corresponding mass spectra of the trimethyl silyl ether derivative, also shown in Table I.

TABLE I

Molecular Weight Information Obtained by (a) Electron Ionization (EI)/Ms and FAB/MS for the parent Compound and Metabolite (Analyzed as the Hydroxy and TMS Derivatives)

| Sample ID | 20 ev | 70 ev | FAB |
|---|---|---|---|
| Parent | $M^+ = 357$ | $M^+ = 357$ | $M + H = 358$ |
| Parent | | | 358.10690 |
| Metabolite | $M^+ = 373$ | $M^+ = 373$ | $M + H = 374$ |
| Metabolite | | | 374.10185 |
| Metabolite TMS | $M^+ = 445$ | — | $M + H = 446$ |

TABLE II

Accurate Mass Measurement and Empirical Formula Established by FAB/MS Using an External Standard, for Parent and Metabolite

| Sample ID | Measured Mass M + H | Empirical Formula | Theoretical Mass |
|---|---|---|---|
| Parent | 358.10690 | $C_{17}H_{17}N_5O_2Cl$ | 358.10707773 |
| Metabolite | 374.10185 | $C_{17}H_{17}N_5O_3Cl$ | 374.10199236 |

The process for preparing the novel compound of this invention comprises condensing the imidazobenzodiazepin-3-amidoxime in the presence of sodium hydride in an anhydrous etherial solvent such as THF with methyl 2-t-butyldimethylsilyloxyisobutyrate by heating for about 4 to 8 hours, followed by hydrolysis of the silyl ether group.

The novel pharmaceutical formulations of this invention comprising the novel compound as active ingredient are prepared by conventional pharmaceutical methods for oral, parenteral or rectal administration and comprise from 0.05 to 100 mg of novel compound per unit dose.

The novel method of treatment of this invention comprises the administration of an effective anxiolytic amount of the novel compound to a patient in need of such treatment. An effective amount comprises about 0.1 to 300 mg/day, and preferably about 1–30 mg/day depending on the patient, e.g. a human, and severity of the anxiety being treated.

EXAMPLE 1

(a)

Methyl 2-t-butyldimethylsilyloxyisobutyrate

To a stirred, chilled (0° C.) solution of methyl-2-hydroxyisobutyrate (20.0 g) in dry $CH_2Cl_2$ was added TBDMS triflate (45 g) dropwise, followed by anhydrous 2,6-lutidine (19.3 g). The mixture was stirred at 0° C. for 1 hour before 150 ml water was added. Stirring was continued for a further hour, the organic layer separated, dried ($Na_2SO_4$), and concentrated to dryness at reduced pressure. The crude product was purified by dry flash silica gel chromatography eluting with $CH_2Cl_2$ to yield the title compound as a colorless oil (30.9 g). $\delta_H$ (360 MHz, $CDCl_3$) 0.07 (6H, s, $Si(CH_3)_2$), 0.87 (9H, s, $C(CH_3)_3$), 1.41 (6H, s, $C(CH_3)_2$), 3.69 (3H, s, $CH_3O$). m/z 233 $(M+1)^+$, 100%, $CI^+$) 217 (30), 174 (40), 164 (45), 106 (30).

(b)

7-Chloro-5,6-dihydro-3-(5-(2-t-butyldimethylsilyloxyisopropyl)-1,2,4-oxadiazol-3-yl)-5-methyl-6-oxo-4H-imidazo[1,5a][1,4]benzodiazepine To a stirred solution of 7-chloro-5,6-dihydro-5-methyl-6-oxo-4H-imidazo[1,5a],[1,4]benzodiazepine-3-amide oxime (19.6 g) and activated molecular sieves (20 g, pellets, 4A) in anhydrous THF (360 ml) was added NaH (1.44 g, 80% dispersion in oil). After 20 minutes, a solution of the silyl protected ester (29.8 g) in THF (40 ml) was added and the mixture brought to reflux for 6 hours. The solution was cooled, glacial acetic acid added (3.8 g) and filtered through hyflo. Solvent was evaporated at reduced pressure and the residue taken up in $CH_2Cl_2$ (220 ml), washed with water (100 ml), brine solution (100 ml), dried ($Na_2SO_4$) and concentrated to dryness at reduced pressure. The resulting oil was purified by silica gel chromatography using 99:1→97:3 $CH_2Cl_2$/MeOH as eluant, to afford the title compound as a yellow oil (11.6 g). $\delta_H$ (360 MHz, $CDCl_3$) 0.00 (3H, s, $SiCH_3CH_3$), 0.01 (3H, s, $SiCH_3CH_3$), 0.86 (9H, s, $C(CH_3)_3$), 1.72 (3H, s, $C-CH_3CH_3$), 1.73 (3H, s, $C-CH_3CH_3$), 3.16 (3H, s, $NCH_3$), 4.44 (1H, d, J=16 Hz, $NCHH$), 5.15 (1H, d, J=16 Hz, $NCHH$), 7.31 (1H, dd, ArH), 7.43–7.56 (2H, m, ArH), 7.98 (1H, s, N=CH).

(c)

7-Chloro-5,6-dihydro-3-(5-(2-hydroxyisopropyl)-1,2,4-oxadiazol-3-yl)-5-methyl-6-oxo-4H-imidazo[1,5a][1,4-]benzodiazepine 7-Chloro-5,6-dihydro-3-(5-(2-t-butyldimethylsilyloxyisopropyl)-1,2,4-oxadiazol-3-yl)-5-methyl-6-oxo-4H-imidazo[1,5a][1,4]benzodiazepine (11.6 g) was stirred in anhydrous THF (300 ml) with tetra-n-butylammonium fluoride (24 ml of 1.0M solution in THF) for 2 hours at room temperature. The mixture was diluted with $CHCl_3$ (250 ml), washed with brine solution (250 ml) and the organic layer was separated. The aqueous layer was extracted with $CHCl_3$ (2×100 ml) and the combined organic extracts dried over $Na_2SO_4$. Solvents were evaporated at reduced pressure and the resulting yellow oil (13 g) was purified by silica gel chromatography eluting with 99:1→98:2 $CH_2Cl_2$/MeOH. The product was further purified by crystallization from hot ethanol to give a white crystalline solid, 5.85 g. The mother liquors, after chromatography and crystallization yielded a further 1.0 g of the title compound m.p. 227° C. (EtOH); HPLC purity 98.9–99.2%; $\delta_H$ (360 MHz, $CDCl_3$) 1.77 (6H, s, $C(CH_3)_2$), 3.22 (3H, s, $NCH_3$), 4.48 (1H, d, J=16 Hz, $NCHH$), 5.13 (1H, d, J=16 Hz, $NCHH$), 7.35 (1H, dd, ArH), 7.52 (1H, t, J=8 Hz, ArH), 7.58 (1H, dd, ArH), 8.03 (1H, s, N=CH).

EXAMPLE 2

Tablets containing the following ingredients are manufactured in the usual manner:

|  | mg/tablet |
| --- | --- |
| Active ingredient | 1 |
| Lactose | 103 |
| Maize starch | 25 |
| Microcrystalline cellulose | 70 |
| Magnesium stearate | 1 |
| Total | 200 |

EXAMPLE 3

Capsules containing the following ingredients are manufactured:

|  | mg/capsule |
| --- | --- |
| Active ingredient | 1 |
| Lactose | 164 |
| Maize starch | 30 |
| Talc | 5 |
| Total | 200 |

The active ingredient lactose and maize starch are mixed in a mixer and then in a comminuting machine. The mixture is returned to the mixer, the talc is added thereto and mixed thoroughly. The mixture is filled by machine into hard gelatine capsules.

EXAMPLE 4

Injection solutions containing the following ingredients are manufactured:

|  | Per ml |  |
| --- | --- | --- |
| Active ingredient | 0.5 | mg |
| Benzyl alcohol | 0.015 | ml |
| Propyleneglycol | 0.4 | ml |
| Ethanol (95 percent) | 0.1 | ml |
| Sodium benzoate | 48.8 | mg |
| Benzoic acid | 1.2 | mg |
| Water per injection q.s. ad | 1.0 | ml |

For the manufacture of 10,000 ml of injection solution, 5 g of the active substance are dissolved in 150 ml of benzyl alcohol and 4000 ml of propylenegycol and 1000 ml of ethanol are added thereto. Then, 12 g of benzoic acid are dissolved in the above mixture and there is added thereto a solution of 488 g of sodium benzoate in 300 ml of water for injection. The solution obtained is brought up to a volume of 10,000 ml by addition of water for injection, filtered and filled into ampoules of suitable size; the residual volume of the ampoules is filled with nitrogen, the ampoules are sealed and sterilized for 30 minutes in an autoclave at 0.7 atmosphere.

EXAMPLE 5

Suppositories containing the following ingredients are manufactured:

|  | g/suppository |
|---|---|
| Active ingredient | 0.001 |
| Cocoa butter (m.p. 36–37°) | 1.255 |
| Carnauba wax | 0.044 |
| Total | 1.3 |

The cocoa butter and carnauba wax are melted in a glass or steel vessel, mixed thoroughly and cooled to 45°. Thereupon, there is added thereto the finely powdered active substance and the mixture is stirred until it is completely dispersed. The mixture is poured into suppository moulds of suitable size, left to cool, the suppositories are removed from the moulds and packed individually in wax paper or metal foil.

What is claimed is:

1. A compound of structural formula:

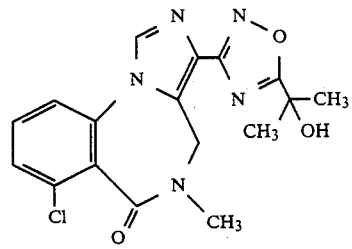

or a pharmaceutically acceptable salt thereof.

2. A pharmaceutical formulation for the treatment of anxiety comprising a pharmaceutical carrier and an anxiolytic amount of the compound of claim 1.

3. A method of treating anxiety comprising the administration of an effective anxiolytic amount of the compound of claim 1 to a patient in need of such treatment.

* * * * *